(12) United States Patent
Nien et al.

(10) Patent No.: US 6,908,766 B2
(45) Date of Patent: Jun. 21, 2005

(54) DEVICE AND METHOD FOR CAPTURING BIOLOGICAL TISSUES

(75) Inventors: Yung-Feng Nien, Taichung (TW); Tsann-Heui Chang, Taichung (TW); Ko-Chang Chen, Tainan (TW); Yeou-Bin Guu, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 10/632,894

(22) Filed: Aug. 4, 2003

(65) Prior Publication Data

US 2004/0077032 A1 Apr. 22, 2004

(30) Foreign Application Priority Data

Oct. 18, 2002 (TW) ........................................ 91124017 A

(51) Int. Cl.⁷ ............................ C12N 11/00; C12M 1/00
(52) U.S. Cl. ................. 435/379; 435/308.1; 435/284.1; 435/29; 435/173.1; 435/173.9; 156/309.6
(58) Field of Search ............................ 435/284.1, 308.1, 435/378, 379, 29, 173.1, 173.9; 156/309.6

(56) References Cited

U.S. PATENT DOCUMENTS

| 5,985,085 A | 11/1999 | Baer et al. |
| 5,998,129 A * | 12/1999 | Schutze et al. ................ 435/4 |
| 6,316,234 B1 | 11/2001 | Bova |
| 2002/0001837 A1 * | 1/2002 | Baer et al. ............... 435/283.1 |

FOREIGN PATENT DOCUMENTS

WO            WO 9939176 A1 *   8/1999   ............ G01N/1/28

* cited by examiner

Primary Examiner—Robert A. Wax
Assistant Examiner—Rosanne Kosson
(74) Attorney, Agent, or Firm—Rabin & Berdo, P.C.

(57) ABSTRACT

A device and method for capturing a biological tissue, comprises cutting a minute biological cellular tissue using a contactless cutting apparatus, wherein, by inverting a biological tissue slide provided with a sample thereon, and after cutting a cellular tissue profile using said contactless cutting apparatus, an impact lever moving mechanism applies from up to down a proper impact force or vibration force onto the target area thus cut, and thereby render said cellular tissue specimen thus captured dropping exactly through a tissue sampling hole into a sampling mortar located therebelow so as to achieve the object of capturing the desired minute biological cellular tissue.

12 Claims, 5 Drawing Sheets

DEVICE AND METHOD FOR CAPTURING BIOLOGICAL TISSUES

BACKGROUND OF THE INVENTION

1. Field of the Invention

The invention relates to a device and method for capturing biological tissues, and particularly, to a non-contact cutting device for cutting microbiological cellular tissue, wherein an appropriate impact force or vibration force is applied in a targeted region from up to down by means of a impact bar displacement mechanism such that the captured cell specimens can pass a tissue sampling hole and drop down exactly into a sampling mortar therebelow.

2. Description of the Prior Art

Since no targeted tissue of very high purity can be obtained by traditional cellular tissue cutting using enzymatic method or fluorescence staining agent, different enzyme or fluorescence agent is needed for hybridization with different tissue cells, and for agents that is scarcely used, the agent has usually a high cost or even is unavailable, advanced study can not be carried out further due to low purity of agents used or due to impurities that can not be removed therefrom.

One conventional tissue capturing device disclosed in U.S. Pat. No. 5,985,085, "METHOD OF MANUFACTURING CONSUMABLE FOR LASER CAPTURE MICRODISSECTION," is characterized in that a tailored film was heated to 80°~90° C. by a IR laser, and after melting a local part, a target tissue was stuck off. Main advantages of its construction comprise: a) a specific method for heating a tailored film, and b) providing of the tailored film. On the other hand, disadvantages of its construction comprise: a) the limitation of the IR heating method being applicable only on a fixed tissue, b) influences on the film by electrostatic force or heating vapor, c) the long pretreatment, d) the fact that only one specimen can be captured once, e) the requirement of preparing a specific film and f) the limitation on the size of tissue removed.

Another conventional tissue capturing device disclosed in U.S. Pat. No. 6,316,234, "LASER CELL PURIFICATION SYSTEM," had a construction characterized in that a target area is labeled through imaging, the unwanted tissue is killed directly, and a specimen slide is removed for examining. The advantage of this device is based on that the unwanted part is killed directly without being captured separately. Main disadvantages of its construction include: a) the area to be processed being too large and hence time-consuming, b) only one specimen being obtainable, and c) contamination of impurity.

Another prior art device and method for tissue capturing is disclosed in U.S. Pat. No. 5,998,129, "METHOD AND DEVICE FOR THE CONTACTLESS LASER-ASSISTED MICROINJECTION, SORTION AND PRODUCTION OF BIOLOGICAL OBJECTS GENERATED IN A PLANAR MANNER". Main features of its construction consisted of: a) movement of the cut target tissue upwardly by a light pressure which is formed by laser till being stuck on a film, and b) self-drop downing of the cellular tissue through gravity. This device had its main advantages as following: a) ability of cutting living tissue, and b) self-drop downing of cellular tissue based on the principle of gravity. However, there are main disadvantages in this construction as: a) more than two kinds of laser sources being needed, b) requirement of the light pressure to overcome the sticking force of the target specimen onto the glass slide, and c) practically, the cut micro-tissue being not able to drop down easily.

Accordingly, the above-mentioned prior arts have many deficiencies, are not of perfect design and need improved at once.

In view of disadvantages derived from the above-described conventional device and method for capturing biological tissues, the inventor of this application had devoted to improve and innovate, and, after an extensive study for many years, has developed successfully the device and method for capturing biological tissue according to the invention.

SUMMARY OF THE INVENTION

One object of the invention is to provide a device and method for capturing biological tissues characterized in that, using the device of the invention, only target tissue cells of interest can be captured, and even smaller organell can be precisely captured, for example, organell of less than 1 $\mu$m can be cut.

Another object of the invention is to provide a device and method for capturing biological tissues, characterized in that the inventive cellular tissue cutting and capturing need not to prepare a lot of related staining agent, thereby pre-treating time prior to capturing can be greatly saved, the gross cost can be lowered, and post-treatment for disposing enzyme and/or staining agent can be eliminated.

Still another object of the invention is to provide a device and method for capturing biological tissues, characterized in that there is no problem associated with the pretreatment for disposing enzyme and/or staining agent, thereby it is not only conducive to the future medical research, but also improve the environment of medical research.

The device for capturing biological tissue that can accomplish the above-described objects comprises:

a non-contact cutting apparatus, comprising a tool for cutting biological cellular tissue through laser beam heating based on the principle of focusing the laser beam into a point such that, as said laser beam point illuminating said biological cellular tissue, the high heat of said laser beam can heat and evaporate said tissue and hence cut said illuminated area to achieve the effect of dissecting and cutting;

a micro-feeding mechanism, for driving a working platform;

a working platform, for fixing a biological tissue slide thereon such that a target tissue to be captured can be labeled through the displaying of a microscope, and, by moving said micro-feeding mechanism and said non-contact cutting apparatus, the cellular tissue can be cut along a profile;

an impact lever moving mechanism, for providing an impact force or vibration force from up to down such that the captured cell or oragnell sample can drop down through a tissue sampling hole into a sampling mortar;

an impact lever linking head, comprising a flexible part provided at the front end of said impact lever moving mechanism for protecting said biological tissue slide, whereby as said impact lever moving mechanism applying an impact force upon said biological tissue slide, said cell or oragnell sample to be captured can drop down;

a biological tissue slide, comprising a flat clear sheet for placing said biological cellular tissue;

a cellular tissue, comprising a tissue of minute biological cell, which, by means of the attraction force between molecules on the surface of biological cell, can generate an adhesive force among each other and onto said biological tissue slide so as to adhere on said biological tissue slide;

a tissue sample protecting means, comprising a thin and flat sheet provided with said tissue sampling hole that penetrates through said means and has a diameter just equal to the diameter of said sampling mortar;

a tissue sampling hole, being provided on said tissue sample protecting means in a manner that, as said impact lever linking head applying from up to down an appropriate impact force or vibration force onto the target region to be captured, said captured cell sample can drop exactly into said sampling mortar located below said target tissue so as to prevent any unwanted cell sample from dropping into said sampling mortar and thus achieve the object of capturing the desired minute biological cellular tissue;

a sampling mortar, for holding said captured cellar tissue specimen; and a controlling circuit, for providing functions of memory, digital signal processing and operation, whereby said controlling circuit can output a signal after operating for controlling said micro-feeding mechanism, driving said working platform and/or said contactless cutting apparatus so as to carry out the procession.

BRIEF DESCRIPTION OF THE DRAWINGS

The drawings disclose an illustrative embodiment of the present invention which serves to exemplify the various advantages and objects hereof, and are as follows.

DETAILED DESCRIPTION OF THE PREFERRED EMBODIMENT

Figure 1:
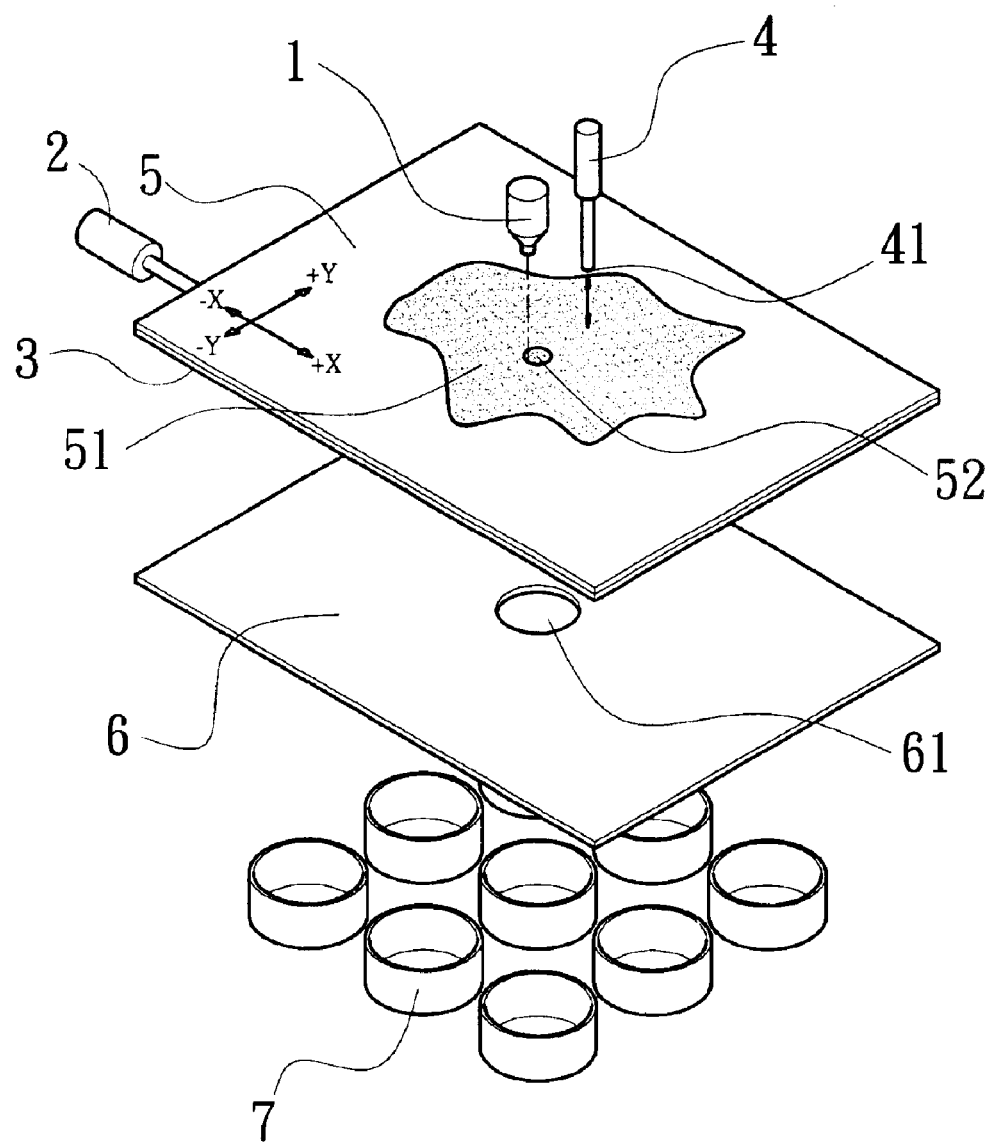
FIG. 1 is a three-dimensional view showing the non-contact cutting apparatus used in the device and method for capturing biological tissues, wherein said apparatus is used to cut a cellular sample by means of a laser beam.
Figure 2:
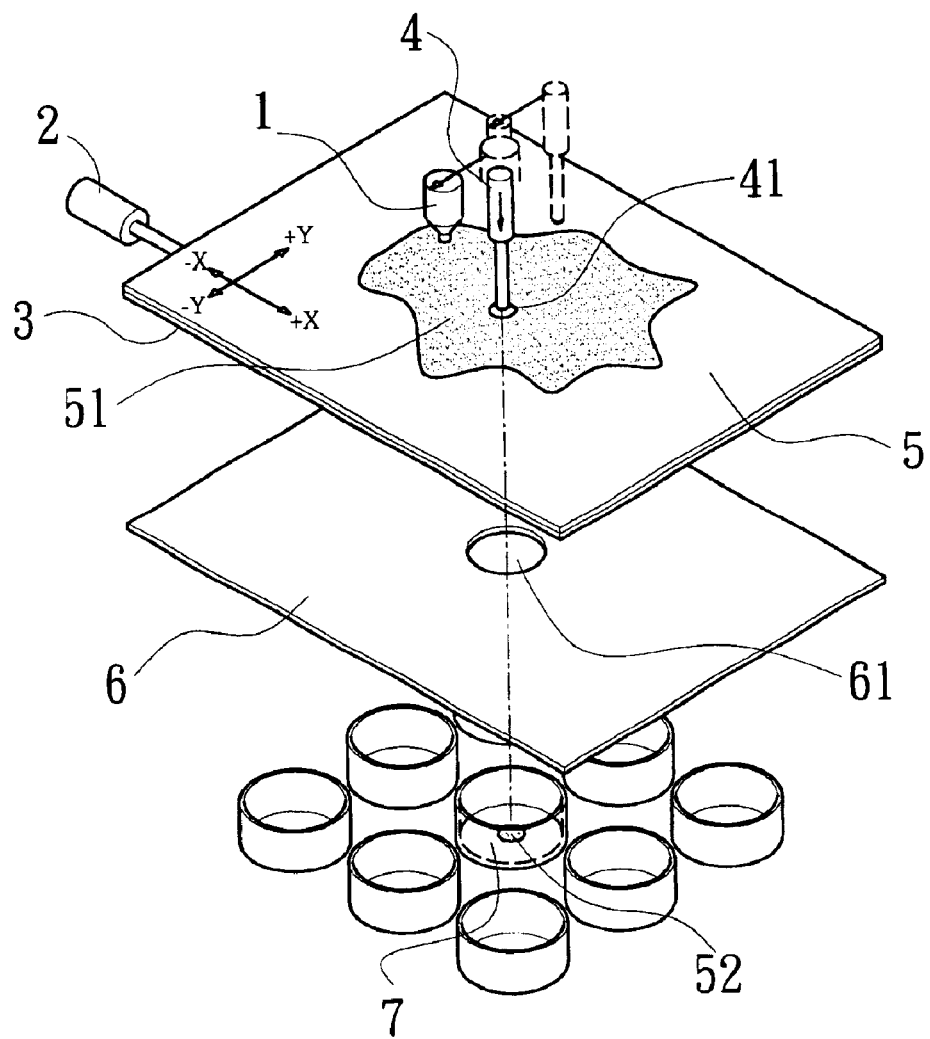
FIG. 2 is a three-dimensional view showing the action of the contactless cutting apparatus used in the device and method for capturing biological tissue shown in FIG. 1 in cutting a cell sample by means of a laser beam and then capturing said cell sample.

Referring to FIGS. 1 and 2, the device for capturing biological tissue provided by the invention comprises essentially: a non-contact cutting apparatus (1) comprising a tool for cutting biological cellular tissue (51) through laser beam heating based on the principle of focusing the laser beam into a point such that, as said laser beam point illuminating said biological cellular tissue (51), the high heat of said laser beam can heat and evaporate said tissue and hence cut said illuminated area to achieve the effect of dissecting and cutting; a micro-feeding mechanism (2), for driving a working platform (3); a working platform (3), for fixing a biological tissue slide (5) thereon such that a target tissue (52) to be captured can be labeled through the displaying of a microscope, and, by moving said micro-feeding mechanism (2) and said contactless cutting apparatus (1), the cellular tissue (51) can be cut along a profile; an impact lever moving mechanism (4), for providing an impact force or vibration force from up to down such that the captured cell sample (52) can drop down through a tissue sampling hole (61) into a sampling mortar (7); an impact lever linking head (41), comprising a flexible part provided at the front end of said impact lever moving mechanism (4) for protecting said biological tissue slide (5), whereby as said impact lever moving mechanism (4) applying an impact force upon said biological tissue slide (5), said cell sample (52) to be captured can drop down; a biological tissue slide (5), comprising a flat clear sheet for placing said biological cellular tissue (51); a cellular tissue (51), comprising a tissue of minute biological cell, which, by means of the attraction force between molecules on the surface of biological cell, can generate an adhesive force among each other and onto said biological tissue slide (5) so as to adhere on said biological tissue slide (5); a tissue sample protecting means (6), comprising a thin and flat sheet provided with a tissue sampling hole (61) that penetrates through said means and has a diameter just equal to or larger than the diameter of said sampling mortar (7); the tissue sampling hole (61), being provided on said tissue sample protecting means (6) in a manner that, as said impact lever linking head (41) applying from up to down an appropriate impact force or vibration force onto the target region to be captured, said captured cell sample (52) can drop exactly into said sampling mortar (7) located below said target tissue so as to prevent any unwanted cell sample from dropping into said sampling mortar (7) and thus achieve the object of capturing the desired minute biological cellular tissue (51); a sampling mortar (7), for holding said captured cellar tissue specimen (52); and a controlling circuit, for providing functions of memory, digital signal processing and operation, whereby said controlling circuit can output a signal after operating for controlling said micro-feeding mechanism (2), driving said working platform (3) and/or said contactless cutting apparatus (1) so as to carry out the procession.

Figure 5:
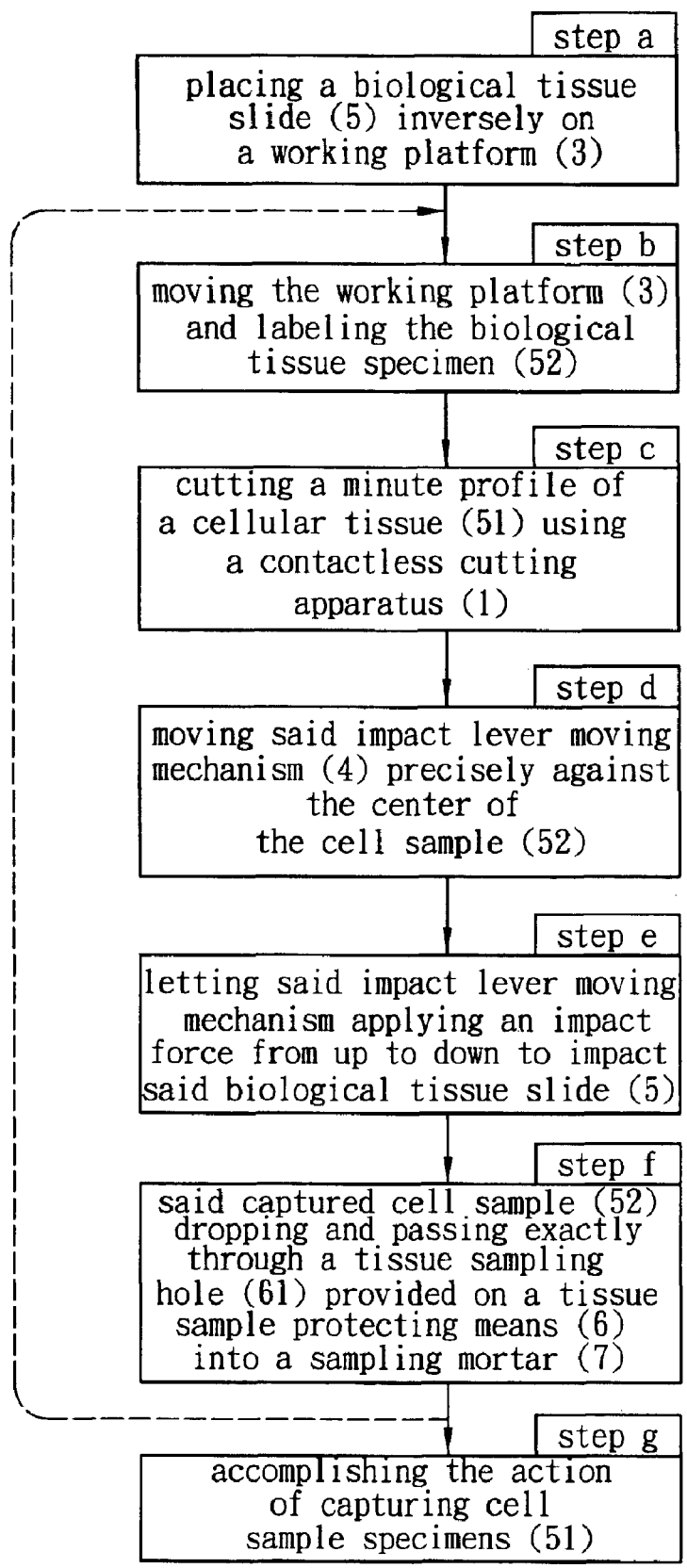
FIG. 5 is a flowchart illustrating the process for capturing a biological tissue using the device and method for capturing biological tissue according to the invention.

Referring to FIG. 5, a flowchart shows the process for carrying out the method of capturing biological tissue according to the invention, which process comprises main steps as follows:

step a: placing a cellular tissue (51) on a biological tissue slide (5) which is made of a glass sheet or a modified membrane glass slide, and then, said biological tissue slide (5) is inverted and fixed on a working platform (3);

step b: amplifying the sample image by a microscope or micro-optics to display the extreme fine structural morphology, labeling the tissue profile of the cell sample

(52) to be captured, and then, through the operation of a controlling circuit, outputting a signal from said controlling circuit to control a micro-feeding mechanism (2), thereby driving said working platform (3) or a non-contact cutting apparatus (1) for carrying out tissue capturing;

step c: after labeling the tissue profile of the cell sample (52) to be captured, and by moving longitudinally or transversely through said micro-feeding mechanism (2), in case of using the laser beam out of said non-contact cutting mechanism (1) to cut a minute profile of a cell sample (possible to cut said cellular tissue (51) to less than 1 μm), said laser beam can transmit said biological tissue slide (5) and focuses the heat of said laser beam onto the profile of said cellular tissue (51) in said cell sample (52) to heat and evaporate it so as to achieve the effect of cutting locally;

step d: in said inverted cellular tissue (51) specimen, via the attraction force between molecules on the surface of biological cell, an adhesive force is generated among each other and onto said biological tissue slide (5) so as to adhere on said biological tissue slide (5); where, after cutting the tissue profile of the cellular sample (52), said controlling circuit will output a signal to control said micro-feeding mechanism (2) and drive said working platform (3) such that the center of said cellular sample thus cut and being able to be captured will move precisely against the impact lever linking head (41) of a impact lever moving mechanism (4);

step e: as soon as the center of the cell sample (52) reaching the impact lever linking head (41) of said impact lever moving mechanism (4), said impact lever moving mechanism (4) applies an impact force or vibration force from up to down to impact said biological tissue slide (5) thereby drop down said captured cell sample (52);

step f: said captured cell sample (52) drops down and passes exactly through a tissue sampling hole (61) provided on a tissue sample protecting means (6), wherein said tissue sample protecting means (6) can prevent un-captured cell sample (51) from dropping into a target sampling mortar (7) so as to achieve the object of capturing the desired minute biological cellular tissue (51); and step g: accomplishing the action of capturing cell sample (51) specimens.

In one embodiment of the invention, said biological tissue capturing apparatus (1) can be used to repeat the cutting and capturing procedures of steps b to f to obtain multiple specimens of cellular tissue (51).

Figure 3:
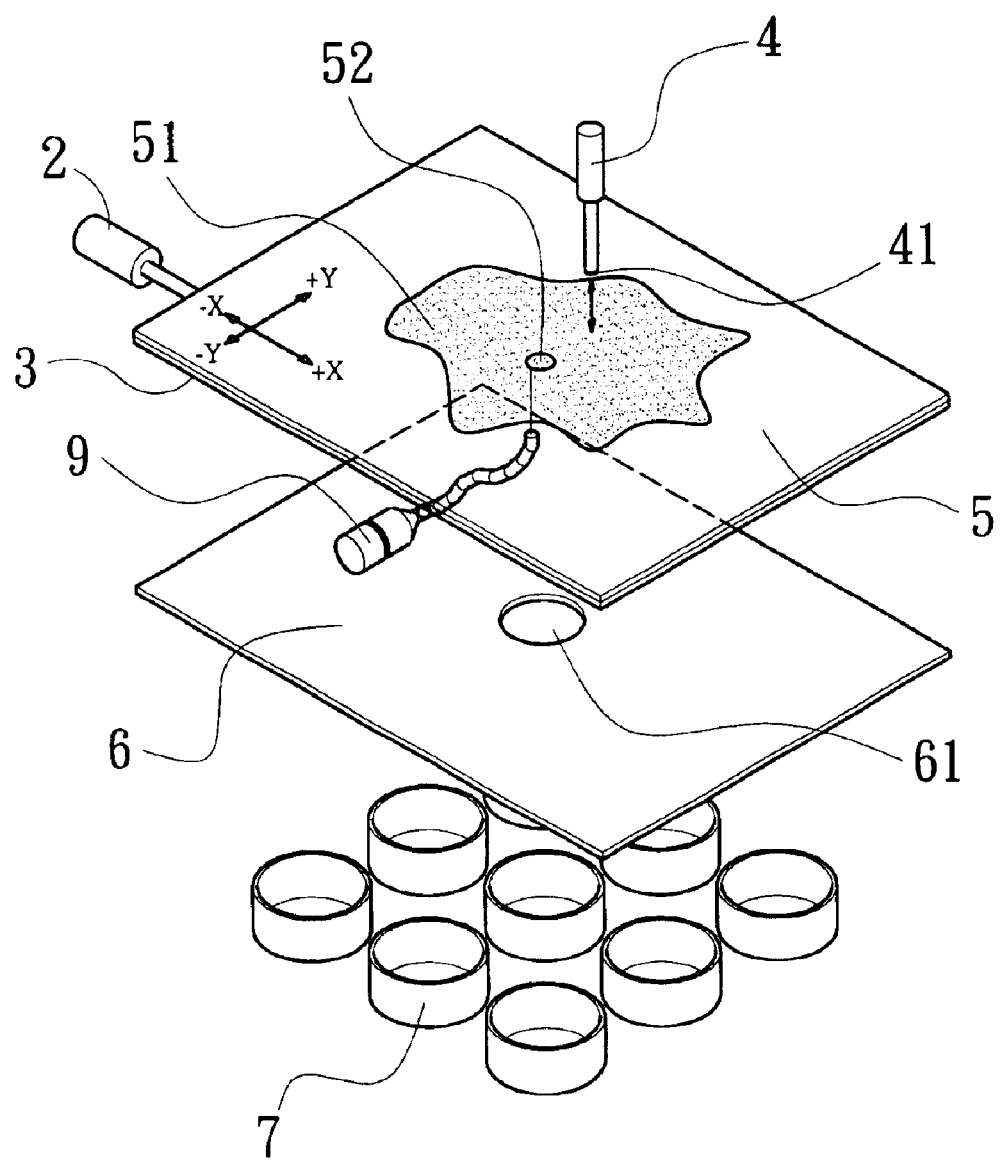
FIG. 3 is a three-dimensional view showing the non-contact cutting apparatus used in the device and method for capturing biological tissues, wherein said apparatus is used to cut a cell sample by means of an air knife.
Figure 4:
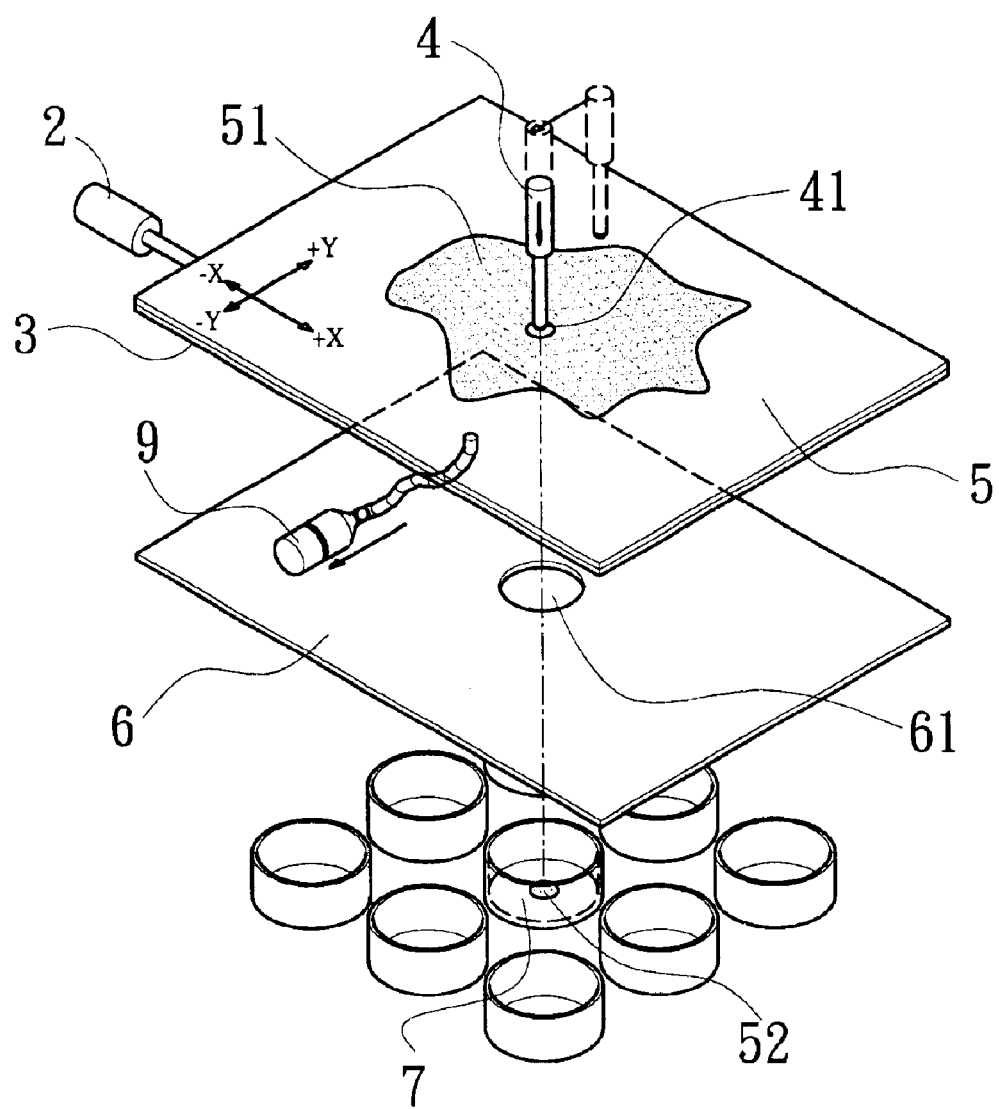
FIG. 4 is a three-dimensional view showing the action of the non-contact cutting apparatus used in the device and method for capturing biological tissue shown in FIG. 3 in cutting a cell sample by means of an air knife and then capturing said cell sample.

In another embodiment of the invention, the non-contact cutting apparatus (1) of the device for capturing biological tissue according to the invention comprises an air knife (9) to cut the cell sample, as shown in the three-dimension view of FIG. 3. In this embodiment, an air knife (9) is used to cut cellular tissue (51) based on the principle of focusing a high pressure air into one point to thereby cut a target cellular tissue (51) as illustrated in more detail below. Said air knife (9) is provided between said biological tissue slide (5) and said tissue sample protecting means (6), and, since the cellular tissue (51) on said biological tissue slide (5) is disposed inversely, said air knife (9) can inject an high pressure air out of a nozzle to cut minute cell sample profile directly in contrast to the laser beam which cut cellular tissue profile (51) by transmitting said biological tissue slide (5).

The device and method for capturing biological tissue provided by the invention has several following advantages over the above-mentioned patents and other conventional techniques:

(1) The device and method for capturing biological tissue provided by the invention takes advantage of a signal output generated through the operation of a controlling circuit to control a micro-feeding mechanism, drive a working platform or a contactless cutting apparatus so as to capture the desired minute biological tissue specimen.

(2) The device and method for capturing biological tissue provided by the invention utilizes a non-contact cutting apparatus to cut a target cellular tissue profile, and then applies a proper impact force from up to down onto the cellular sample thus captured to render said cell sample drop into a sampling mortar.

(3) When the device and method for capturing biological tissue provided by the invention is used to capture a cellular tissue, as the impact lever linking head applies a proper impact force or vibration force from up to down onto the cellular sample thus captured to render said cell sample drop down, said cellular sample will pass through a tissue sampling hole provided on the tissue sample protecting means to render it drop precisely into the sampling mortar in a manner that said sample tissue protecting means can prevent the non-target tissue from dropping into the target sampling mortar and thereby achieve the object of capturing the minute biological cellular tissue.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for capturing biological tissues, comprising:

placing a biological tissue sample on a biological tissue slide;

after said placing is performed, inverting said biological tissue slide and fixing said biological tissue slide on a working platform, so that the biological tissue sample is disposed between the biological tissue slide and the working platform;

positioning the biological tissue slide, with the tissue sample disposed thereunder, above a flat planar tissue sample protecting means, said tissue sample protecting means having a tissue sample hole therein;

defining a tissue profile from the tissue sample;

cutting along the tissue profile to form a cell sample from the tissue sample, using a contactless cutting apparatus which is an air knife;

after cutting along the tissue profile, driving said working platform such that a center of the cell sample is disposed under an impact lever moving mechanism; and applying a force to said biological tissue slide with the impact lever moving mechanism, thereby causing said cell sample to drop down through the tissue sample hole and into a sampling mortar.

2. A device for capturing biological tissues, comprising:

a working platform;

a biological tissue slide adapted to receive a biological tissue sample thereon, said biological tissue slide being fixed to said working platform in an inverted state, so that the biological tissue sample is disposed between the biological tissue slide and the working platform;

a contactless cutting apparatus for cutting a cell sample along a defined tissue profile from the biological tissue sample, the contactless cutting apparatus being an air knife;

a micro-feeding mechanism, for driving said working platform;

an impact lever moving mechanism, for providing a force to said biological tissue slide a flat sheet tissue sample protecting means, under said working platform, and having a tissue sampling hole therein, the tissue sampling hole being disposed under the cell sample; and a sampling mortar disposed under said tissue sampling hole, wherein said sampling mortar has a diameter larger than a diameter of said tissue sampling hole, so that when said impact lever moving mechanism provides the force to the biological tissue slide, said cell sample drops through the tissue sampling hole and into said sampling mortar, while preventing any unwanted biological tissue sample from dropping into said sampling mortar.

3. The method as recited in claim 1, further comprising outputting a control signal to control at least one of said cutting apparatus, driving of said working platform, and memory functions.

4. The method as recited in claim 1, further comprising repeating the recited operations.

5. The method as recited in claim 1, wherein said tissue sample hole has a larger diameter than a diameter of said sampling mortar.

6. The method as recited in claim 1, wherein said impact lever has a flexible linking head.

7. The method as recited in claim 1, wherein a controlling circuit is used in driving the working platform.

8. The method recited in claim 1, wherein said force is an impact force.

9. The method recited in claim 1, wherein said force is a vibrational force.

10. The device as recited in claim 2, wherein said impact lever moving mechanism includes a flexible lever linking head.

11. The device as recited in claim 2, wherein said force is an impact force.

12. The device as recited in claim 2, wherein said force is a vibrational force.

* * * * *